United States Patent [19]

Claypool

[11] Plant 4,956

[45] Nov. 23, 1982

[54] APPLE TREE

[76] Inventor: Lucian D. Claypool, 631 W. 5th St., Ontario, Calif. 91762

[21] Appl. No.: 216,421

[22] Filed: Dec. 15, 1980

[51] Int. Cl.[3] ..... A01H 5/03
[52] U.S. Cl. ..... Plt./34
[58] Field of Search ..... Plt./34

*Primary Examiner*—Robert E. Bagwill

*Attorney, Agent, or Firm*—Brown & Martin

[57] ABSTRACT

A new and distinct variety of apple tree that grows vigorously and yields a rich harvest under the undesirable climatic conditions of coastal Southern California. The fruit of the tree ripens early and has a tart flavor. The fruit has a small core with few or no seeds. The flesh of the fruit resists discoloration and deterioration for several hours after being sliced.

6 Drawing Figures

The present invention relates to a new and distinct variety of apple tree. I discovered the original tree in a mature, cultivated state growing in the yard of Esther Bollman, at 604 East H St., Ontario, Calif. Although the parentage is unknown, it most likely is the Newtown Pippin.

My attention was attracted to the original tree because of its early leafing and blooming in the spring after an unusually mild winter. Although most potential pollinators were delayed two months by the mild winter, this tree nevertheless had a fair crop of apples. Such performance indicates that this tree does not require as much winter chill to break its dormancy as do most apple trees.

The original tree has thrived in the Ontario, Calif. area even though this area frequently is beset by heavy smog. Although disease resistance is largely dependent upon the condition of the root stock, the original tree has never shown any signs of disease.

The tree leafs out and blooms in early spring with heavy foliage and bears fruit which ripens in early-August. Some of the fruit hangs on the tree until mid-September. The tree tends to bloom simultaneously and the fruit tends to ripen on the tree simultaneously, thereby reducing expenses for spraying pesticides and harvesting. The relatively early ripening of the fruit enables the fruit to be brought to market earlier than the fruit of most other apple trees.

The tree has heavy foliage throughout the hot summer months and thereby is an ideal shade tree.

The fruit is excellent for cooking and canning. It also is good for eating as it has a slightly tart but pleasant flavor. The fruit has an unusually small core and has few or no seeds. One of the outstanding characteristics is the tendency of the flesh of the fruit to remain fresh without discoloration or deterioration for several hours after being sliced.

The refrigeration and shipping qualities of the fruit appear to be excellent thereby enhancing the potential for sales of the fruit.

I have asexually reproduced this new and distinct variety of apple tree by summer budding on existing root stock and on trees in Ontario, Calif.; and the reproduced trees appear to be true to the original tree. The tree is extremely easily budded, even on root stock as small as $\frac{1}{4}$ inch diameter. Buds started on July 4th grew to approximately three feet by Sept. 4th, even with the temperature frequently over 100 degrees Fahrenheit and with frequent heavy smog.

The tree and its fruit are shown in the Drawing, in which some of the distinguishing characteristics may be observed.

The following is a detailed description of the characteristics of this new and distinct apple tree.

Figure 1:
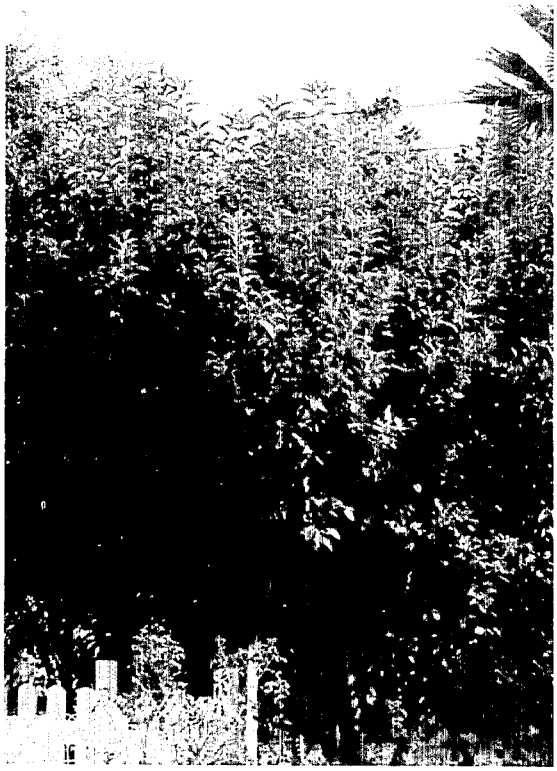
FIG. 1 shows the original tree in the foregound with its thick foliage, and having new branches near the top that tend to grow straight up without support.

The original tree is a semi-dwarf. Possibly this is because of its tight bark, which may be due to the low relative humidity that is prevalent in Ontario. The tree has a rounded and spreading top. New branches tend to grow straight up without support, as shown in FIG. 1. The tree has the characteristics of spur-type trees in that it has very dense vigorous and rapidly growing foliage, as is also shown in FIG. 1.

Figure 2:
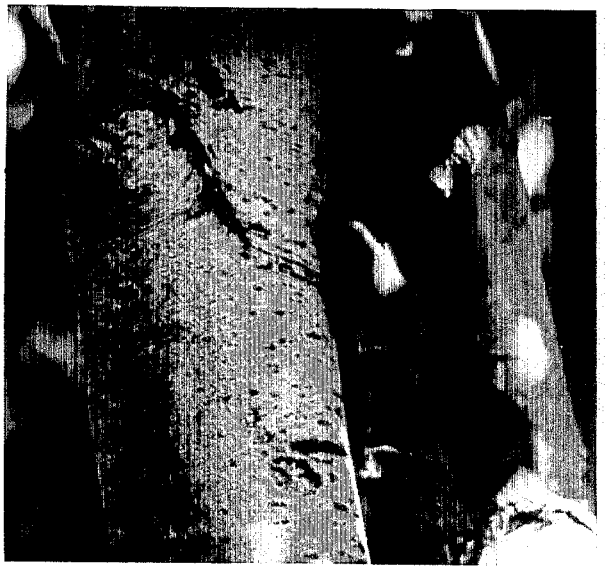
FIG. 2 shows a trunk of the original tree.

The tree has a medium-sized smooth grayish-white trunk with a light purple blush and yellow faded streaks as shown in FIG. 2.

The branches of the tree are medium thick and smooth.

The stems of the branches of the tree are medium-size, have fine pubescence, and bud approximately one inch apart.

Figure 3:
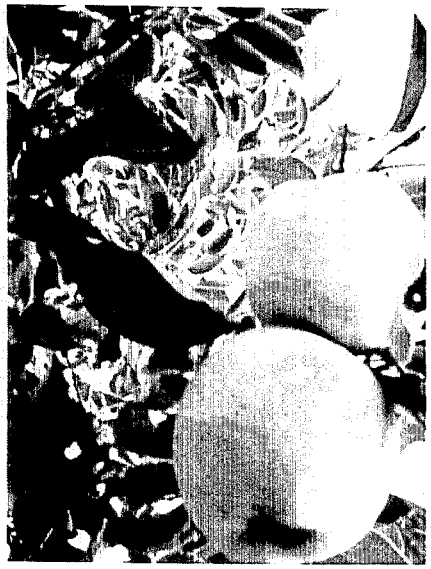
FIG. 3 shows ripened fruit hanging on the original tree among the foliage.

The leaves of the tree are oval as shown in FIGS. 1, 2 and 3. They are of medium length and are slightly serrated. The petiole is of medium thickness. The size of the leaves varies with the average leaf being approximately $2\frac{3}{4}$ inches in width by $4\frac{1}{2}$ inches in length.

Figure 4:
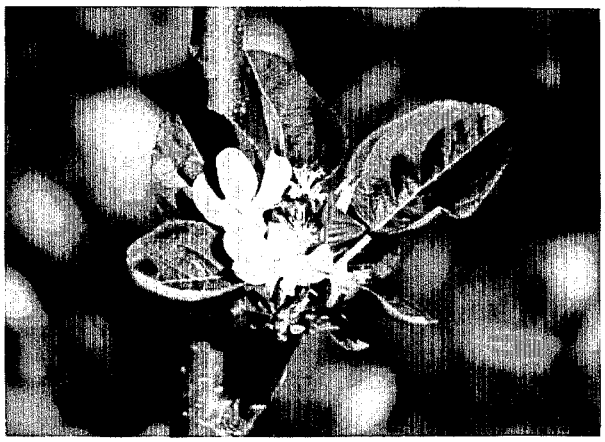
FIG. 4 shows blossoms on one of the reproduced trees.

The blossoms are white, as shown in FIG. 4. The blossom is approximately one inch across. The calyx of the blossom is partially open, with some quite small segments persisting. The blossoms bloom in mid-March.

The fruit ripens in early-August with a heavy yield. Some apples hang on the tree until mid-September.

The skin of the fruit is thin, smooth, glossy and waxed. The skin is a light yellowish-green upon ripening and acquires a reddish blush as it matures, due to exposure to direct sunlight as shown in FIG. 3. The apple having the more reddish color shown in FIG. 5 hung high in the tree until mid-September and become more reddish due to more exposure to direct sunlight. Color designations are with reference to the Exotica Horticultural Color Guide, wherein light yellowish-green is color number 79 (citron) and red is color number 32 (crimson).

Figure 5:
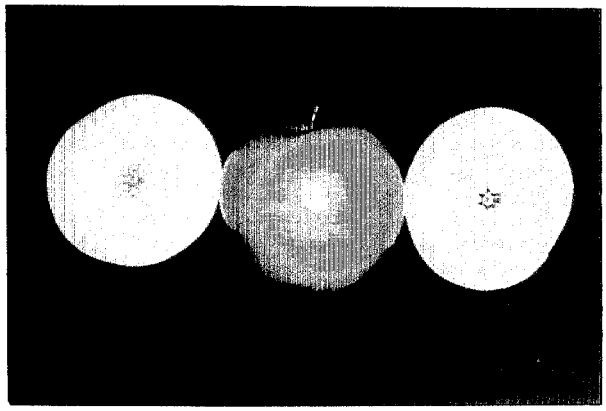
FIG. 5 shows a whole ripened apple from the tree together with a ripened apple from the tree that was bisected, showing its interior having an unusually small core.
Figure 6:
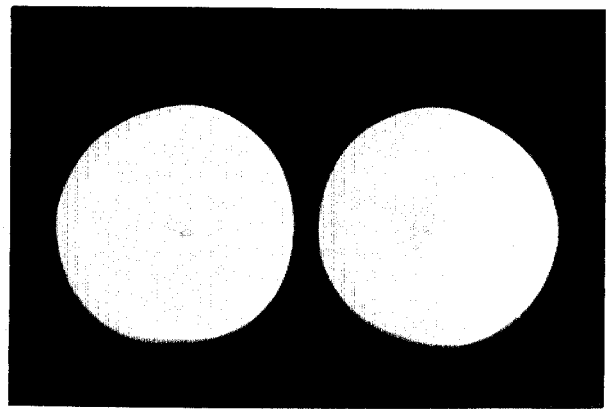
FIG. 6 shows another ripened apple from the tree that was bisected, showing its interior having almost no core. This apple had only one seed.

The flesh of the fruits is white, tender, crisp and firm with a fine grain, as shown in FIGS. 5 and 6. The flesh is medium, juicy and remains fresh without discoloration or deterioration for several hours after being sliced.

The flavor of the fruit has a fair sugar acid balance and is slightly tart. The flavor enables the fruit to be used for cooking, fresh eating and salads.

The fruit has a mild and sweet aroma.

The calyx of the fruit is pubescent on the outer side.

The fruit has a form-axial diameter averaging about $3\frac{1}{4}$ inches and a transverse diameter averaging about $3\frac{1}{2}$ inches.

The fruit is fairly round and slightly oblate at the base with slight lobes around the basin, as shown in FIGS. 3 and 5.

The stem of the fruit is medium in length and width.

The cavity of the fruit has an average depth of about $\frac{1}{2}$ inch and an average breadth of about $\frac{3}{4}$ inch. The cavity is partially brownish unwaxed color.

The basin of the fruit has an average depth of about $\frac{3}{8}$ inch and an average breadth of about $\frac{5}{8}$ inch. The basin is slightly pubescent. The shape of the basin is dependent upon the quantity of seeds, and varies accordingly.

The lenticels of the fruit are moderately prominent.

The core of the fruit is unusually small and frequently seedless. A typical small core is shown in FIG. 5. An extremely small core is shown in FIG. 6 had only one seed. Typically, the apples have about five seeds on the average.

I claim:

1. A new and distinct variety of apple tree, substantially as herein shown and described, characterized by its vigorous growth and harvest under undesirable climatic conditions, the tart flavor and early ripening of its fruit, the unusually small core of its fruit, and the resistance of the flesh of its fruit to discoloration and deterioration upon being sliced.

* * * * *